United States Patent
Ando et al.

(10) Patent No.: US 7,582,348 B2
(45) Date of Patent: Sep. 1, 2009

(54) COMPOSITE EXTENSIBLE MEMBER AND METHOD OF MANUFACTURING THE SAME

(75) Inventors: Kenji Ando, Tochigi (JP); Kenji Kobayashi, Tochigi (JP)

(73) Assignee: Kao Corporation, Tokyo (JP)

( * ) Notice: Subject to any disclaimer, the term of this patent is extended or adjusted under 35 U.S.C. 154(b) by 294 days.

(21) Appl. No.: 10/569,204

(22) PCT Filed: Sep. 2, 2004

(86) PCT No.: PCT/JP2004/012723

§ 371 (c)(1),
(2), (4) Date: Feb. 23, 2006

(87) PCT Pub. No.: WO2005/025789

PCT Pub. Date: May 24, 2005

(65) Prior Publication Data

US 2006/0270302 A1 Nov. 30, 2006

(30) Foreign Application Priority Data

| Sep. 8, 2003 | (JP) | ............................. 2003-316010 |
| Jan. 30, 2004 | (JP) | ............................. 2004-024747 |
| May 14, 2004 | (JP) | ............................. 2004-144270 |

(51) Int. Cl.
*B32B 9/00* (2006.01)
*B32B 5/12* (2006.01)
*A61F 13/15* (2006.01)
*D04H 1/00* (2006.01)

(52) U.S. Cl. .................. 428/103; 428/105; 442/381; 442/328; 442/329; 604/358

(58) Field of Classification Search .......... 442/327–329, 442/334, 381; 428/103, 105
See application file for complete search history.

(56) References Cited

U.S. PATENT DOCUMENTS

| 6,291,039 | B1 | 9/2001 | Combe et al. |
| 6,468,630 | B1 | 10/2002 | Mishima et al. |
| 2003/0144643 | A1* | 7/2003 | Jarpenberg et al. ..... 604/385.24 |

FOREIGN PATENT DOCUMENTS

| JP | 7-144383 A | 6/1995 |
| JP | 2518953 A | 9/1996 |
| JP | 2000-279444 A | 10/2000 |
| JP | 2001-11769 A | 1/2001 |
| JP | 2001-504899 A | 4/2001 |
| JP | 2001-157690 A | 6/2001 |
| JP | 2002-653 A | 1/2002 |
| JP | 2002-291799 A | 10/2002 |
| WO | WO-03/059603 A | 7/2003 |

\* cited by examiner

*Primary Examiner*—Lynda Salvatore
(74) *Attorney, Agent, or Firm*—Birch, Stewart, Kolasch & Birch, LLP

(57) ABSTRACT

An extensible composite member (1) including an extensible portion (10) having two sheet materials (2, 3) and elastic members (4) intermediate between the sheet materials. The two sheet materials (2, 3) are discontinuously bonded to each other in the extending direction of the extensible portion (10) (X direction) and a direction perpendicular thereto (Y direction). The elastic members (4) are arranged in the extensible portion (10) avoiding joints (5) between the sheet materials and have both ends thereof fixed to the sheet materials. Each of the two sheet materials (2, 3) forms folds (6) continuously running across a plurality of the elastic members (4).

14 Claims, 8 Drawing Sheets

COMPOSITE EXTENSIBLE MEMBER AND METHOD OF MANUFACTURING THE SAME

TECHNICAL FIELD

The present invention relates to an extensible composite member and a method of making the same.

BACKGROUND ART

In the field of absorbent articles including disposable diapers and sanitary napkins, it is a practice widely adopted to bond an elastic member in its stretched state to a sheet material and allow the elastic member to contract thereby to make gathers (an extensible portion with a large number of folds) of the sheet.

JP-A-2001-11769 (reference-1) discloses an elastically extensible sheet having a flat sheet material accordion-folded to make a large number of folds and elastic members bonded to the top of a plurality of the folds.

Japanese Utility Model 2518953 (reference-2) discloses a disposable diaper having an elastically extensible portion having a sheet material of nonwoven fabric folded back into two layers and an elastic member sandwiched between the two layers. The sheet material is joined to itself along linear joints extending in a direction perpendicular to the extending direction of the elastic member, and the elastic member is bonded to the sheet material at the joints.

DISCLOSURE OF THE INVENTION

The folds of conventional general gathers have a short length in the direction perpendicular to the extending direction, and the appearance is not so neat.

The sheet of reference-1 has each fold crossing a plurality of the elastic members and is relatively pleasant to the eye. However, the feel to the touch of the folds is not so good on account of the joints between the sheet material and the elastic members.

The elastically extensible portion described in reference-2 is not very soft in the direction parallel with the linear joints between the sheet material layers due to the joints and therefore leaves room for improvement in softness and feel to the skin.

The present invention provides, in its first aspect, an extensible composite member having an extensible portion composed of two sheet materials and a plurality of elastic members disposed between the sheet materials. The two sheet materials are discontinuously bonded to each other in the extending direction of the extensible portion and a direction perpendicular thereto. The elastic members are arranged in the extensible portion avoiding the joints between the sheet materials and have both of their ends fixed to the sheet materials. Each of the two sheet materials forms a plurality of folds continuously running across a plurality of the elastic members.

The present invention also provides, in its second aspect, a method of making the extensible composite member. The method includes the step of arranging a plurality of elastic members in their stretched state on a first sheet material and superposing a second sheet material on the side of the first sheet material having the elastic members on, the step of partly joining the first and second sheet materials in their superposed state in an area where the elastic member is absent, the step of subjecting the first and the second sheet materials with the elastic members there between to a process for fixing the elastic members to the first and the second sheet materials along places spaced apart from each other in the extending direction of the elastic members, and the step of allowing the elastic members to contract to cause each of the first and the second sheet materials to form a plurality of folds.

The present invention provides, in its third aspect, an extensible composite member composed of two sheet materials and a plurality of elastic members disposed between the sheet materials. The two sheet materials are discontinuously bonded to each other in the extending direction of the elastic members and a direction perpendicular thereto to form joint lines each composed of joints in each of the two directions. At least two of the elastic members are each disposed to overlap each of the joints composing the joint line in the extending direction and fixed between the sheet materials at the individual joints. The sheet materials each form folds between the joint lines in the direction perpendicular to the extending direction.

The present invention provides, in its fourth aspect, a method of making the extensible composite member of the third aspect. The method includes the steps of disposing a plurality of elastic members in their stretched state between two sheet materials and partly heat-pressing the superposed sheet materials with a plurality of projections to partly fusion bond the sheet materials to form the above-described joints. The step of partly heat-pressing is carried out in a manner that does not result in cutting the elastic members.

The present invention provides, in its fifth aspect, an extensible composite member having two sheet materials and a plurality of elastic members disposed between the sheet materials. The two sheet materials are partly bonded to each other to form joints. The joints line up to make joint lines in a direction crossing the extending direction of the elastic members. A part of the joint lines and another part of the joint lines are different in positions of their joints (making up each joint line) in a direction (Y direction) crossing the extending direction (X direction). Each of the elastic members is fixed between the sheet materials in at least part of the joints. The sheet materials each form folds between every two adjacent joint lines.

The present invention provides, in its sixth aspect, a method of making the extensible composite member of the fifth aspect. The method includes the steps of disposing a plurality of elastic members in their stretched state between two sheet materials and partly heat-pressing the superposed sheet materials with a plurality of projections to partly fusion bond the sheet materials to form the above-described joints. The step of partly heat-pressing is carried out in a manner that does not result in cutting the elastic members.

BRIEF DESCRIPTION OF THE DRAWINGS

FIG. 13($b$) illustrates a pattern of arranging joints in still another embodiment of the fifth aspect of the present invention, in which the longitudinal direction of the individual joints does not coincide with the running direction of the joint lines.

BEST MODE FOR CARRYING OUT THE INVENTION

Preferred embodiments of the first and the second aspects of the present invention will be described with reference to the accompanying drawings.

Figure 1:
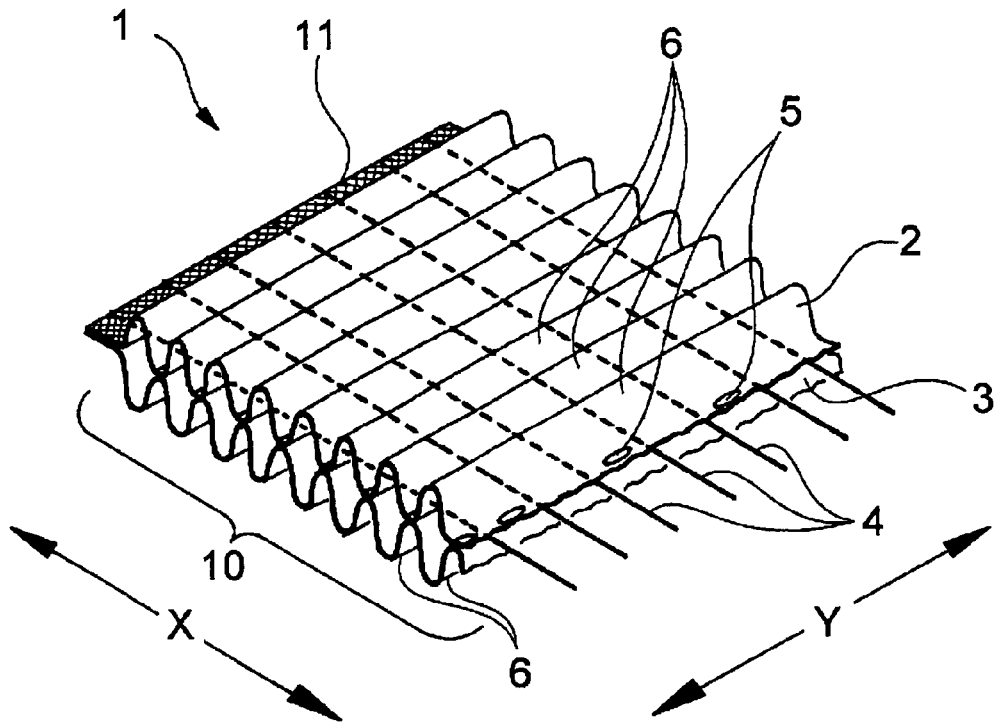
FIG. 1 is a perspective of an extensible composite member according to an embodiment of the first aspect of the present invention, with a part cut away.

As illustrated in FIG. 1, an extensible composite member 1 according to an embodiment (first embodiment) of the first aspect of the present invention has an extensible portion composed of two sheet materials 2 and 3 and a plurality of elastic members 4 disposed between the two sheets.

The extensible portion 10 is formed in a central portion of the extensible composite member 1 in the elastic members 4 extending direction. The elastic members 4 are joined to the sheet materials at both end portions 11 (only one of the end portions is shown) of the extensible composite member 1 in that direction.

Figure 2:
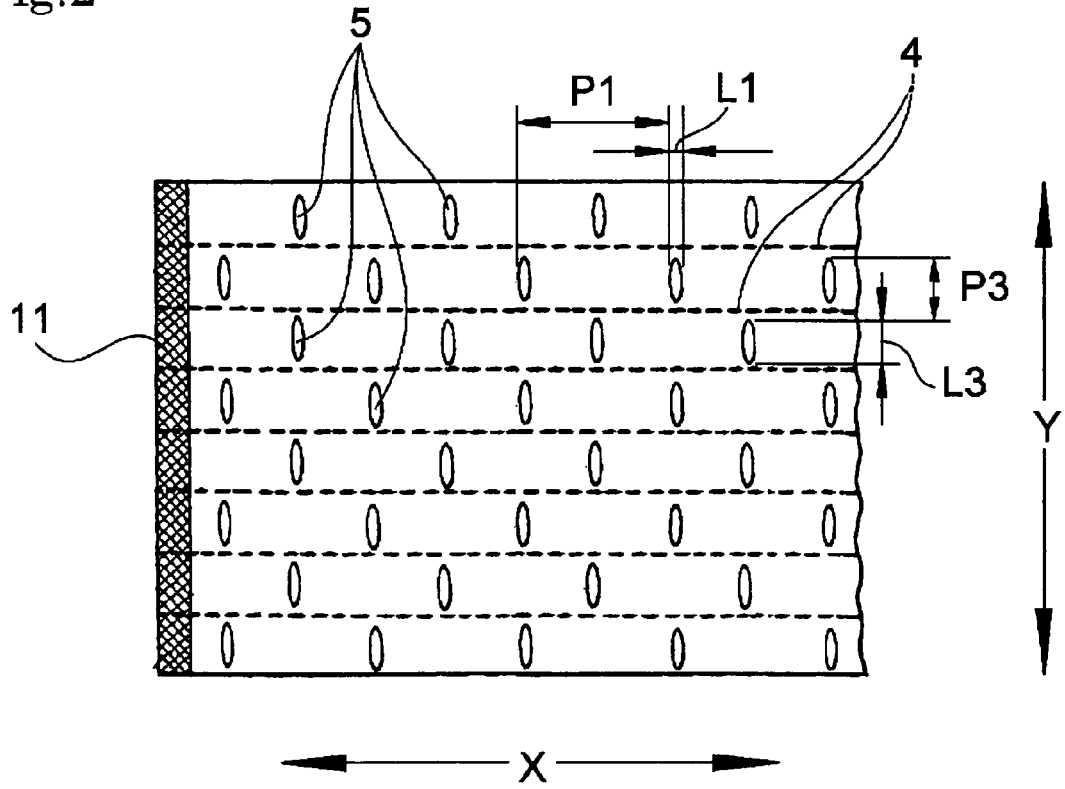
FIG. 2 is a plan of the extensible composite member of FIG. 1 with the extensible portion extended.

As illustrated in FIG. 2, the two sheet materials 2 and 3 composing the extensible portion 10 are fusion bonded (joined) to each other discontinuously in both the extensible portion 10 extending direction (X direction) and a direction perpendicular thereto (Y direction).

In the first embodiment, the elastic members 4 are arranged parallel to each other so as to extend in the longitudinal direction of the extensible composite member 1.

When elastic members are parallel with each other as in the present embodiment, the extensible portion 10 extending direction is the same as the elastic members 4 extending direction. When elastic members 4 are not parallel with each other, the extensible portion extending direction is a direction perpendicular to the direction of folds (hereinafter described) running across a plurality of elastic members.

FIG. 2 illustrates a pattern of forming fusion bonded parts (joints) between the two sheet materials 2 and 3. As illustrated, in the first embodiment, the fusion joints 5 are in a staggered pattern.

In order to assure formation of folds 6 continuously extending across a plurality of the elastic members 4, it is preferred that the fusion joints 5 be arranged at a pitch P1 (see FIG. 2) of 1 to 30 mm, more preferably 6 to 20 mm, in the extensible portion 10 extending direction (X direction) with the extensible portion being in the extended state (the state presented in FIGS. 2 or 3); that the individual fusion joints 5 have a length L1 (see FIG. 2) of 0.1 to 5 mm, more preferably 0.2 to 1.5 mm in the same direction in the same state; and that the ratio of the pitch P1 to the length L1 (P1/L1) be in the range of from 1.1 to 300, more preferably from 4 to 100.

It is preferred that the two sheet materials 2 and 3 not be joined to each other in the extensible portion 10 at places except the fusion joints 5.

Each of the elastic members 4 is arranged in the extensible portion 10 avoiding the fusion joints 5 of the two sheet materials, and fixed to the sheet materials 2 and 3 only at its ends. Both ends of the elastic members 4 are fixedly held in between the sheet materials 2 and 3 at the respective end portions 11 of the extensible composite member 1 (only one of the end portions 11 is depicted in the figures). The two end portions 11 may be formed as extensible end portions.

The fusion joints 5 of the sheet materials are arranged to line up (to make sealing lines) in the extending direction of the extensible portion 10 (X direction) and in a direction perpendicular thereto (Y direction). The fusion joints 5 lining in the perpendicular direction are placed every two adjacent elastic members.

There is a region with no fusion joint 5 between a line of fusion joints 5 in the extensible portion 10 extending direction (X direction) and an adjacent line of fusion joints 5. The region continuously extends between the two end portions 11 (only one of which is shown) of the extensible composite member 1. The elastic member 4 is disposed but not fixed along that region. The positions of fusion joints 5 in a line in the extensible portion extending direction (X direction) are shifted by half pitch (P½) from those in an adjacent line.

When the extensible composite member 1 of the first embodiment is in a relaxed state (with no external force applied), the elastic members 4 contract. As a result, the two sheet materials 2 and 3 each form a plurality of folds 6 continuously running across the elastic members 4.

The folds 6 of the sheets 2 and 3 project on the respective sides of the extensible composite member 1. Each fold 6 has a curved surface whose cross-section is arc-shaped at the top. The curved surface continues in the Y direction perpendicular to the extensible portion extending direction. In the present embodiment, two folds 6 are created between every two fusion joints 5 that are adjacent in the extensible portion extending direction (X direction). Every fold 6 continuously runs in the Y direction perpendicular to the extensible portion extending direction without being cut at positions where it crosses the elastic members 4.

The extensible composite member 1 of the first embodiment has a very beautiful appearance since a large number of the folds 6 created by contraction of the elastic members 4 individually continue in the direction (Y direction) perpendicular to the extensible portion 10 extending direction. If the sheet materials 2 and 3 are continuously joined (by, for example, fusion bonding or adhesion with an adhesive) along the elastic members 4, the folds 6, particularly the crest of the folds 6, would be depressed where they overlap the elastic members 4, resulting in formation of random folds. Such randomness not only impairs neatness to the eye but also reduces freedom of deformation of the folds 6 under external force, which reduces softness to the touch.

In the extensible composite member 1 of the first embodiment, the individual elastic members 4 in the extensible portion 10 are present between the valleys of every two adjacent folds 6 formed of the sheet material 2 and the valleys of every two adjacent folds 6 formed of the other sheet material 4. The elastic members 4 are not bonded to these valleys of either the sheet material 2 or 3 as well as the other part of the sheet materials 2 and 3. Furthermore, the sheet materials 2 and 3 are not continuously joined to each other in the extensible portion 10 in either the extensible portion 10 extending direction or the perpendicular direction. Being so configured, the extensible composite member 1 avoids an increase in stiffness and allows the folds 6 to be deformed with more freedom under external force. Additionally, the folds have a curved surface at the top. Therefore, the extensible composite member 1 has an increased volume in the thickness direction and feels extremely soft and pleasant when touched.

Since the elastic members in the extensible portion 10 are not fixed to either the sheet material 2 or 3, the amount of an adhesive to be used can be minimized or reduced to zero. Particularly when the sheet materials 2 and 3 are joined together by fusion bonding as in the present embodiment, the effect in reducing the adhesive is outstanding. Reduction of a hot-melt adhesive assures breathability and moisture permeability.

Materials making the extensible composite member 1 of the first embodiment are described below.

Materials that can be used as the sheet materials 2 and 3 include nonwoven fabrics fabricated by various processes, such as air-through nonwoven, heat-rolled nonwoven, hydroentangled nonwoven, spun-bonded nonwoven, and melt-blown nonwoven, woven fabrics, knitted fabrics, resin films, and composite laminate sheets composed of two or more of these sheet materials.

To create folds pleasant to the eyes and to the touch, it is desirable to use air-through nonwoven fabric, heat-rolled nonwoven fabric, hydroentangled nonwoven fabric, spun-bonded nonwoven fabric or melt-blown nonwoven fabric as both the two sheet materials or at least one of them, especially the one that is to come into direct contact with the skin where the extensible composite member is designed to be applied to the skin.

The sheets are deformed with the contraction of the elastic members to form folds. That is, the stiffness of the sheets is one of the factors decisive of the fold formability of the extensible composite member and the cushioning properties of the folds formed. The stiffness of a sheet material can be represented in terms of buckling strength.

The sheet material used in the present invention (inclusive of the first to sixth aspects) preferably has a buckling strength of 100 cN or lower, more preferably 70 cN or lower. The buckling strength as referred to herein can be measured with a Tensilon universal tensile tester from Orientec Corp. in compressive mode as follows.

Buckling Strength Testing Method (CD):

Test pieces measuring 150 mm in the machine direction (MD) and 30 mm in the direction crossing the machine direction (CD) are cut out of a sample and each formed into a 45 mm diameter cylinder by rolling. The overlapped ends were stapled together at their upper and lower parts to make specimens. Measurement is taken with the Tensilon universal tensile tester in compressive mode under measuring conditions of a rate of compression of 10 mm/min and a measuring distance of 20 mm in a measuring environment of 20° C. and 65% RH. The maximum strength of the specimen when compressed by 20 mm is read for every specimen to obtain an average, which is taken as the buckling strength of the sample.

As stated, nonwoven fabric is a preferred sheet material. Nonwoven fabric as a sheet material preferably has a weight of 5 to 50 $g/m^2$, more preferably 18 to 30 $g/m^2$. Nonwoven fabric having a weight in that range preferably has a buckling strength of 50 cN or lower, more preferably 30 cN or lower, in the CD and of 70 cN or lower, more preferably 50 cN or lower, in the MD.

The material making the sheet material (e.g., fiber of nonwoven fabric or a film forming material of a resin film) preferably comprises a heat fusible resin, such as polyethylene and polypropylene. The fiber constituting nonwoven fabrics can be sheath-core conjugate fibers having a heat fusible resin only in the sheath.

The material of one of the two sheet materials and the material of the other sheet material may be the same or different.

The two sheet materials used in the present invention inclusive of the first to sixth aspects do not need to be separate sheets. A single sheet material can be folded to make two facing panels, one of which serves as a first sheet material, and the other as a second sheet material.

Any known elastic materials of various kinds that have been used in absorbent articles such as disposable diapers and sanitary napkins can be used with no particular limitation as a material making the elastic members 4. Examples include synthetic rubbers such as styrene-butadiene, butadiene, isoprene and neoprene, natural rubber, EVA, stretch polyolefins, and polyurethane. Forms of the elastic members include a thread with a rectangular, square, circular or polygonal section, tape, or multifilamentous yarn.

Another factor decisive of fold formability of the extensible composite member is a stretch ratio and a stretch stress of the elastic member. The elastic member is required to have a prescribed stretch ratio and stretch stress in order to create folds with a protruding cross-section. The elastic member is disposed between the sheet materials in a stretched state at a stretch ratio preferably of 20% to 1000%, more preferably 50% to 400%. On the elastic members' contracting, the excess of the nonwoven fabric in the portion having gathered protrudes outward, i.e., away from the fusion joints to form folds with a protrudent cross-section.

The height of the folds, which is of importance considering fold formability and cushioning properties, can be designed freely by selecting the pattern of arrangement and the pitch of the joints, the material, and the elastic members. The height of the folds is preferably about 1 to 15 mm per side. High folds can be created to provide an extensible composite member with a soft and voluminous hand feel by spacing the joints at a predetermined interval and by stretching the elastic members to a stretch ratio sufficient to gather the spaced joints to form protrudent folds. In order to form folds with a height h on one side, the distance between adjacent joints is preferably 2×h at the least. When the distance is the least (2×h), it is desirable for the elastic member to contract such that the adjacent joints come into contact with each other.

Among preferred elastic members is a natural rubber (or synthetic rubber) member. A natural (or synthetic) rubber member is desirably a low modulus element having a thickness of 0.05 to 1.5 mm and a width of 0.2 to 5 mm. A preferred stretch stress varies depending on the cross-sectional area. As a typical example, it is preferred to use a monofilament of 0.35 mm in thickness and 0.91 mm in width having a stress at 100% elongation usually of about 1 to 70 g, preferably of about 1 to 40 g, more preferably of about 1 to 30 g. A plurality of elastic members with such stress characteristics are used in the extensible composite member.

Also included in preferred elastic members is Spandex fiber (elastic polyurethane fiber). A monofilamentous Spandex fiber having a fineness preferably of 10 to 3360 denier, more preferably of 70 to 1120 denier, is used. "Denier" is a unit of thickness of a yarn. A yarn weighing one gram per 9,000 meters is one denier. A plurality of such Spandex elastic fibers are used at a stretch ratio of 30% to 500%.

An extensible composite member that softly extends and contracts and has beautiful folds can be obtained by disposing a plurality of monofilaments of the above-described low modulus elastic member at a high stretch ratio preferably of 100% or higher, more preferably of 200% or higher.

The aforementioned extensible composite member 1 is produced efficiently and economically by, for example, the following method, which is an embodiment of the second aspect of the present invention.

A plurality of elastic members 4 are disposed parallel to each other in their stretched state on a sheet material 2, and another sheet material 3 is superposed on the elastic members side of the sheet material 2.

The sheet materials superposed on each other are fusion bonded in parts in a region where the elastic members 4 are absent by heat embossing, ultrasonic embossing or like means. Heat embossing or ultrasonic embossing is carried out by, for example, introducing the two sheet materials into the nip between an embossing roll having projections in a pattern corresponding to the pattern of arrangement of the fusion joints 5 (see FIG. 2) and a backup roll.

The two sheet materials having the elastic members 4 therebetween are then subjected to a uniting process for fixing the elastic members 4 to both the sheet materials 2 and 3 along portions spaced apart in the elastic members 4 extending direction. The uniting process is a process by which the elastic members are joined to both the sheet materials 2 and 3 and includes heat embossing and ultrasonic embossing. The uniting process may be a process in which an adhesive is applied to one or both of the two sheet materials and/or the elastic members and pressing the adhesive-applied parts. The adhesive is applied to, for example, the sheet material 2 before disposing the elastic members 4 thereon, or the sheet material 3 before being overlaid on the sheet 2, or the elastic members 4 before or after being disposed on the sheet material 2.

The sheet materials 2 and 3 with the elastic members 4 therebetween is cut across so that the portions having been subjected to the uniting process may be positioned at both ends of the cut part in the elastic members 4 extending direction. The elastic members 4 are let to contract to make each of the sheet materials 2 and 3 create folds. The extensible composite member 1 having the above-described configuration is thus obtained.

Another embodiment (second embodiment) of the first aspect of the present invention in which an extensible composite member 1' is provided will then be described. The second embodiment will be illustrated with reference to differences from the first one. Elements identified with the same numerals as in the first embodiment may be identical and will not be redundantly described. To those particulars that are not described here is applied the description of the extensible composite member 1.

Figure 3:
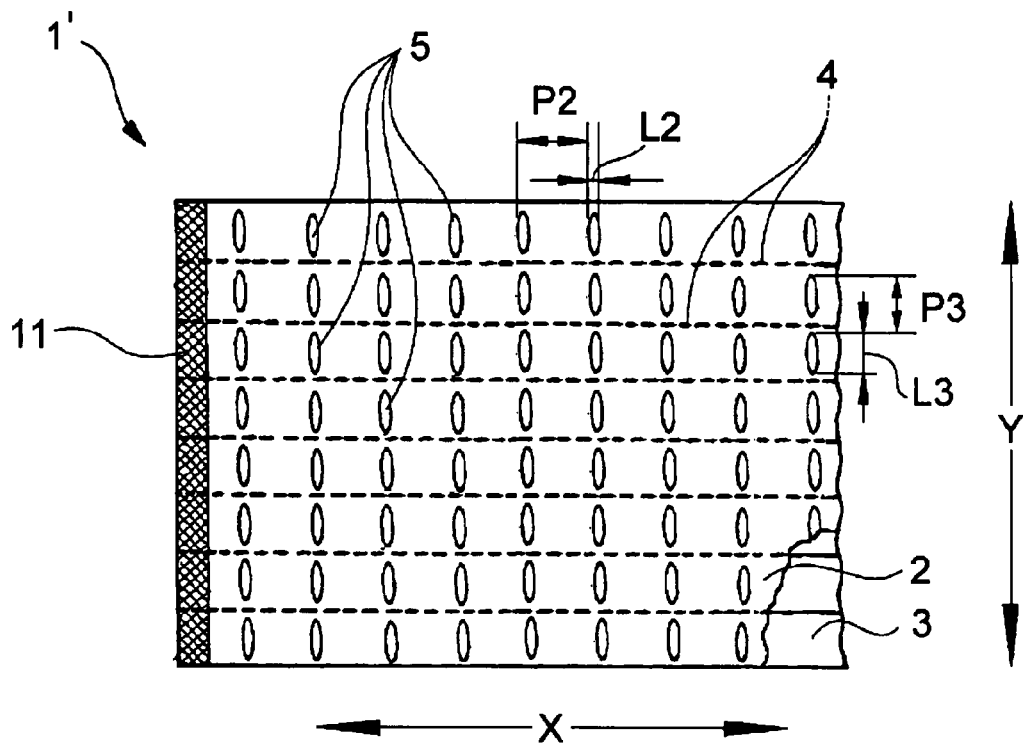
FIG. 3 illustrates an extensible composite member according to another embodiment of the first aspect of the present invention (corresponding to FIG. 2).

As shown in FIG. 3, in the extensible composite member 1', fusion joints 5 between the sheet materials 2 and 3 are arranged to line up in both the extending direction of the extensible portion 10 (X direction) and a direction perpendicular thereto (Y direction). The fusion joints 5 lining in the perpendicular direction are placed between every two adjacent elastic members 4.

When the extensible composite member 1' of the second embodiment is in a relaxed state (with no external force applied), the elastic members 4 contract, whereby the two sheet materials 2 and 3 each gather to form a plurality of folds 6 continuously running across the elastic members 4 similarly to the first embodiment. Thus, the extensible composite member 1' exerts the same action and effect as with the extensible composite member 1.

In the second embodiment, one fold 6 is created between every two fusion joints 5 that are adjacent in the extensible portion extending direction (X direction).

In order to assure formation of folds 6 continuously running across a plurality of the elastic members 4, it is preferred that the fusion joints 5 be arranged at a pitch P2 (see FIG. 3) of 1 to 20 mm, more preferably 3 to 10 mm, in the extensible portion 10 extending direction (X direction) with the extensible portion 10 being in the extended state; that the individual fusion joints 5 have a length L2 (see FIG. 3) of 0.1 to 5 mm, more preferably 0.2 to 1.5 mm in the same direction in the same state; and that the ratio of the pitch P2 to the length L2 (P2/L2) be in the range of from 1.1 to 200, more preferably from 2 to 50.

In the above-illustrated extensible composite members 1 and 1', especially the extensible composite member 1, it is preferred that the pitch P3 (see FIGS. 2 and 3) of the fusion joints 5 in the direction (Y direction) perpendicular to the extensible portion 10 extending direction be 1 to 40 mm, more preferably 2 to 15 mm; that the length L3 (see FIGS. 2 and 3) of the individual fusion joints 5 be 0.5 to 20 mm, more preferably 1 to 10 mm in that direction; and that the ratio of the pitch P3 to the length L3 (P3/L3) be in a range of from 1.05 to 80, more preferably of from 1.05 to 15.

The third and fourth aspects of the present invention will be described based on their preferred embodiments by way of the drawings.

Figure 5:
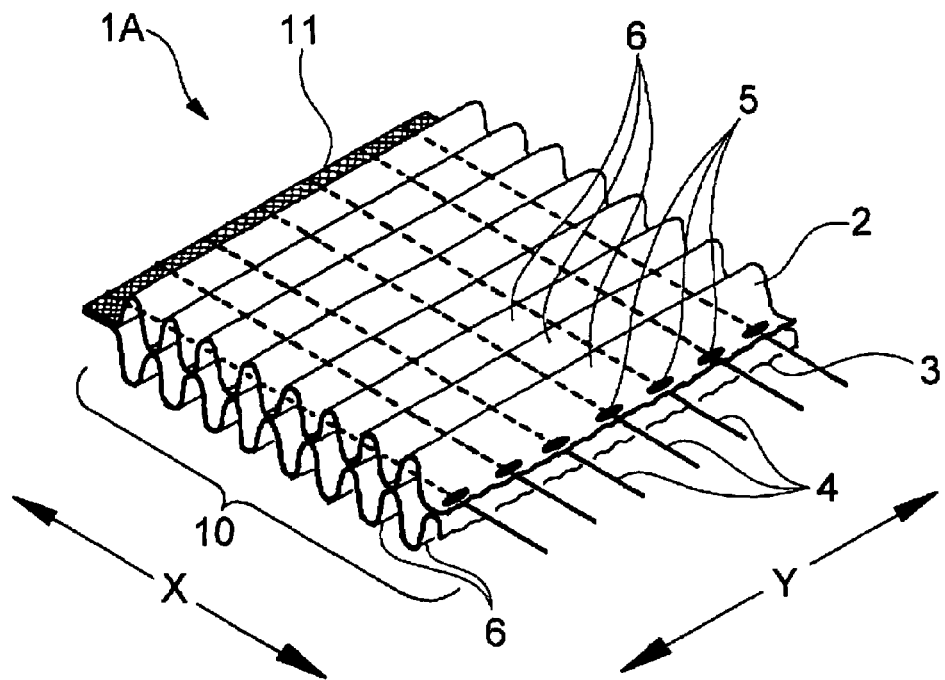
FIG. 5 is a perspective of an extensible composite member according to an embodiment of the third aspect of the present invention, with a part cut away.
Figure 6:
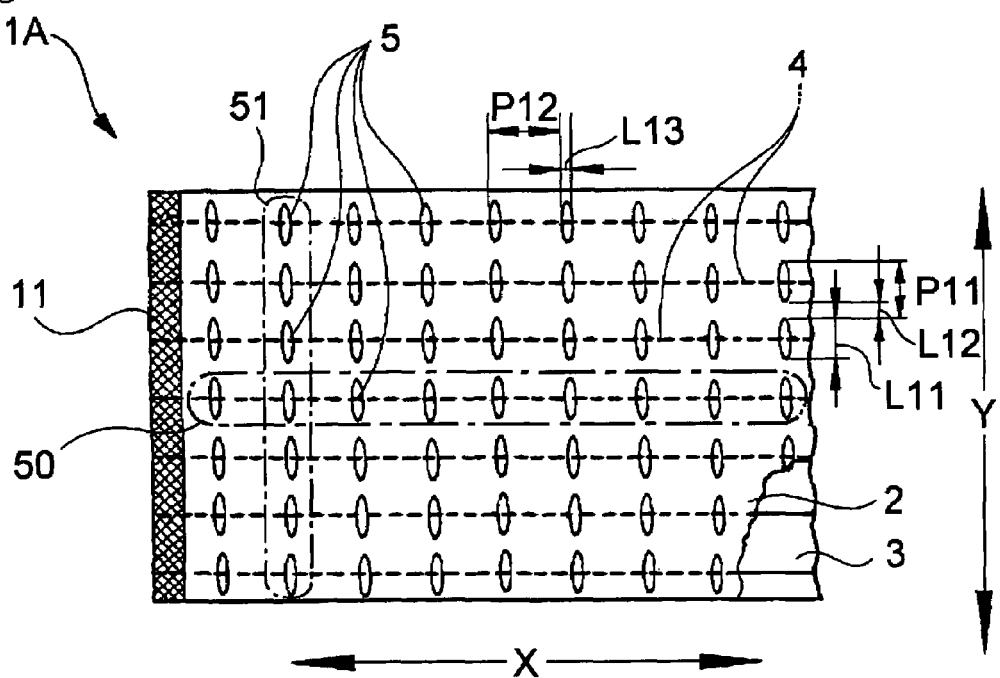
FIG. 6 is a plan of the extensible composite member of FIG. 5 with the elastic members extended to stretch flat.

FIGS. 5 and 6 illustrate an extensible composite member 1A according to an embodiment of the third aspect of the present invention. As shown, the extensible composite member 1A is composed of two sheet materials 2 and 3 and a plurality of elastic members 4 disposed therebetween.

The extensible composite member 1A is rectangular in its plan view. The extensible composite member 1A has an end seal 11 at both ends thereof (only one end is illustrated) in the extending direction of the elastic members 4 (i.e., the direction of arranging each elastic member 4), each end seal 11 being continuous in the direction perpendicular to the elastic members 4 extending direction. All the elastic members 4 are fixed between the sheet materials 2 and 3 in the end seals 11. The portion of the extensible composite member 1A except the end seals 11 is an extensible portion 10.

As illustrated in FIG. 6, the sheet materials 2 and 3 are discontinuously fusion bonded joined) to each other in both the extending direction of the elastic members 4 (X direction) and a direction perpendicular to that direction (Y direction). "Direction crossing the extending direction of the elastic members 4" as will be referred to herein denotes a direction unparallel with the extending direction of the elastic members 4, making a certain angle with the extending direction. In this particular embodiment, the crossing direction is a direction perpendicular to the extending direction, i.e., Y direction. The crossing angle being taken as 90° when the crossing direction is perpendicular to the elastic members 4 extending direction as in the present embodiment, the crossing direction preferably makes an angle of 75° to 105°, more preferably 85° to 95°, even more preferably 90°.

In the present embodiment, the elastic members 4 are arranged parallel to each other. When elastic members are parallel with each other, the direction of extension (stretch) and contraction of the elastic members 4 is the same as the running direction of the elastic members 4. When elastic members 4 are not parallel with each other, the elastic members 4 extending and contracting direction is a direction perpendicular to the running direction of folds 6 (hereinafter described).

As illustrated in FIG. 6, the extensible composite member 1A has a plurality of (seven in the embodiment illustrated) joint lines 50, only one of which is indicated by numeral 50, each of which includes a plurality of fusion joints 5 lining up in the elastic members 4 extending direction (X direction). It also has a plurality of joint lines 51, only one of which is indicated by numeral 51, each of which includes a plurality of fusion joints 5 lining up in the direction perpendicular to the elastic members 4 extending direction (Y direction).

The joint lines 50 in the elastic members 4 extending direction (X direction) are parallel to each other. So are the joint lines 51 in the direction perpendicular to the extending direction (Y direction). There is a region with no fusion joint 5 between every two fusion lines 50 in the X direction. The region continuously extends between the two end seals 11 (only one of which is shown) of the extensible composite member 1A.

It is preferred for improving softness that the joint lines in a direction crossing the elastic members 4 extending direction (Y direction in the case of the present embodiment) each have a ratio of a pitch P11 (see FIG. 6) of arranging the fusion joints 5 to a length L11 (see FIG. 6) of the individual fusion joints (P11/L11) ranging from 1.05 to 80, more preferably 1.05 to 15, and that the pitch P11 of arranging the fusion joints be from 1 to 40 mm, more preferably 2 to 15 mm.

From the same viewpoint, the length L11 is preferably 0.5 to 20 mm, more preferably 1 to 10 mm, and the length L12 (see FIG. 6) between the adjacent fusion joints in that joint line is preferably 0.5 to 30 mm, more preferably 1 to 20 mm.

In order to assure formation of folds 6, especially folds 6 continuously running across a plurality of the elastic members 4 and therefore beautiful to the eye, it is preferred that the fusion joints 5 be arranged at a pitch P12 (see FIG. 6) of 1 to 30 mm, more preferably 2 to 15 mm, in a joint line along the elastic members 4 extending direction (X direction); that the individual fusion joints 5 have a length L13 (see FIG. 6) of 0.1 to 5 mm, more preferably 0.2 to 1.5 mm in that direction; and that the ratio of the pitch P12 to the length L13 (P12/L13) be in the range of from 1.1 to 300, more preferably from 4 to 100.

The above-recited dimensions and ratios are measured with the extensible composite member being in a stretched flat state by stretching the elastic members (a state in which the extensible composite member is stretched out to the same dimension as reached when it is flattened with any influences of the elastic members excluded by, for example, cutting the elastic members) as illustrated in FIG. 6.

In the present embodiment, all the elastic members 4 are each disposed to overlap every fusion joint 5 forming a joint line 50 in the elastic members 4 extending direction (X direction). Each elastic member 4 passes the middle of the individual fusion joints 5 in the Y direction and fixed between the sheet materials 2 and 3 at each fusion joint 5 without being cut at the fusion joints 5.

When the extensible composite member 1A of the present embodiment is in a relaxed state (with no external force applied), the elastic members 4 contract, whereby the two sheet materials 2 and 3 each form a plurality of folds 6 between every two adjacent joint lines in the direction crossing the elastic members 4 extending direction (Y direction) as shown in FIG. 5.

The folds 6 of the sheets 2 and 3 project on the respective sides of the extensible composite member 1A. Each fold 6 has a curved surface whose cross-section is arc-shaped at the top. Every fold 6 continuously runs in the perpendicular direction (Y direction) across the elastic members 4 without being cut at positions where it crosses the elastic members 4. Therefore, the folds 6 are very beautiful to the eye.

Since the elastic members 4 are fixed between the sheet materials 2 and 3 at the fusion joints 5 forming the joint lines 50 along the elastic members 4 extending direction (X direction), the contracting stress of the elastic members 4 is used to securely gather the two sheet materials between every two adjacent fusion joints in every joint line 50. Therefore, uniformity that is not to be impaired can be achieved among the folds 6 formed. Moreover, since the joint lines 51 along the direction crossing the elastic members 4 extending direction (Y direction) are each formed of spacedly arranged fusion joints 5, the extensible composite member 1A is very soft and flexibly deformable by, for example, a force compressing the extensible composite member 1A in the Y direction or a force curving the extensible composite member 1A along the Y direction. Therefore, where the extensible composite member 1A is used in an absorbent article as a member making gathers (an extensible portion with a large number of folds), particularly as a member forming standing gathers (standing anti-leak cuffs), the gathers are soft and pleasant to the touch and less irritating to the skin.

In the extensible composite member 1A of the present embodiment, the individual elastic members 4 are present between the valleys of every two adjacent folds 6 formed of the sheet material 2 and the valleys of every two adjacent folds 6 formed of the other sheet material 3. Additionally, the folds have a curved surface at the top. Therefore, the extensible composite member 1A has an increased volume in the thickness direction and feels extremely soft and pleasant when touched.

Materials that can be used to make the elements constituting the extensible composite member 1A include those described with respect to the extensible composite member 1. Unless inconsistent with the context, the description of the materials making the extensible composite member of the first aspect of the invention applies to the extensible composite member of the third aspect.

In the present embodiment, too, the sheet materials 2 and 3 are deformed with the contraction of the elastic members 4 to form folds 6. Similarly to the extensible composite member 1, the stiffness of the sheet materials 2 and 3 is an important factor decisive of the fold formability of the extensible composite member and the cushioning properties of the folds formed, and another factor decisive of the fold formability of the extensible composite member is a stretch ratio and a stretch stress of the elastic members. The preferred constitution of the extensible composite member 1 explained above in connection with these factors (e.g., the buckling strength of the sheet materials, the stretch of the elastic members when disposed between the sheet materials, and the height of the folds) also applies to the extensible composite member 1A.

Where nonwoven fabric is chosen as a sheet material, it is preferred to use nonwoven fabric having a weight of 5 to 50 g/m², more preferably 8 to 30 g/m². Nonwoven fabric having a weight in that range preferably has a buckling strength of 50 cN or lower, more preferably 30 cN or lower, in the CD and of 70 cN or lower, more preferably 50 cN or lower, in the MD. To use such soft sheet materials secures fold formability.

The aforementioned extensible composite member 1A is produced efficiently and economically by, for example, the following method.

Figure 7:
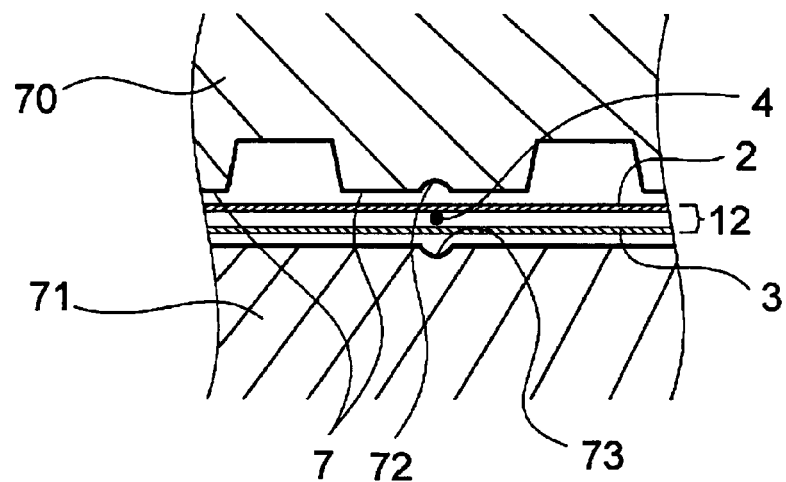
FIG. 7 is a fragmentary cross-section of an embosser useful to make an extensible composite member of the types shown in FIGS. 5 and 10.

A plurality of elastic members 4 are disposed in their stretched state between two sheet materials 2 and 3 to prepare a laminate 12 in which the two sheet materials are not joined together. The laminate 12 is partly fusion bonded by heat-pressing with projections 7 arranged in the pattern of fusion joints 5 (see FIG. 6) as illustrated in FIG. 7. Care should be taken not to cut the elastic members 4 in the partial heat pressing. In order for the two sheet materials to be fusion bonded together and, at the same time, for the elastic members 4 to be fusion bonded, without being cut, to the sheet materials via the heat fusible fiber present in the sheet materials, it is preferred to create optimum conditions by controlling three parameters: (1) pressing pressure of the projections 7 to the anvil roll 71, (2) clearance between the projections 7 and the anvil roll 71, and (3) temperature of the projections 7 and the anvil roll 71. It is also effective for preventing the elastic members from being cut to select a material unsusceptible to the influences of pressure and heat, i.e., a cutting-resistant material as elastic members and to set the stretch ratio of the elastic members rather low as the product specification.

It is possible to positively reduce the pressure imposed to the elastic members. Means for reducing pressure application include measures to avoid pressure application to where the projections 7 cross the elastic members. For example, the anvil roll receiving the projections may be made of rubber, e.g., silicon rubber. Where durability of rubber is a problem, rubber may be applied only to the parts on which the elastic members are pressed. Another example is to use projections each having a groove (depression) 72 for pressing pressure reduction along where the elastic member 4 is disposed. Heat fusion using such projections can be effected, e.g., with a heat embosser or an ultrasonic embosser by introducing the laminate 12 into the nip between an embossing roll 70 with the projections 7 on its peripheral surface and a facing anvil roll (backup roll) 71.

The embosser illustrated in FIG. 7 additionally has grooves (depressions) 73 for pressing pressure reduction on the peripheral surface of the anvil roll 71, on which the laminate 12 is pressed under the projections 7, along where the elastic members are present.

By making a groove 72 and/or grooves 73 for pressing pressure reduction on the projections for fusion bonding and/or the facing surface, the elastic members 4 can easily be fixed in the fusion joints 5 without being cut. The parts of the elastic member 4 in the fusion joint 5 may be merely held between the two sheet materials but with tightness so as not to move between the two sheet materials or may have the surface thereof fusion bonded to one or both of the sheet materials. The grooves for pressing pressure reduction can be provided on either one or both of the projections and facing surface.

In a preferred mode, grooves for pressing pressure reduction are provided not on the projections of the embossing roll but on the anvil roll only. A sheet is introduced along the surface of the anvil roll, and the elastic members 4 are introduced along the anvil roll via the sheet so that they may fit in the respective grooves for pressing pressure reduction. Fusion bonding is performed with the elastic members positioned in the grooves so as not to move in the CD. That is, with the sheet being wrapped around the anvil roll, the elastic members are placed along the position of the grooves. By so doing, high positioning precision in the CD can be achieved in sealing the two sheet materials by pressing with the projections across the grooves on the anvil roll. Achievement of high positioning precision provides freedom of design of the seal pattern, making it feasible to produce a more fit-to-use extensible composite material.

The depth of the groove for pressure reduction is suitably such that the elastic member sandwiched between the sheet materials in the sketched state may fit into the groove. Where the elastic member fits neatly into the groove, the sheet materials can be heat sealed at positions on each side of the elastic member without damaging the elastic member. Tight fit of the elastic member provides resistance against the elastic member's contraction and keeps the elastic member in the position without allowing the elastic member to get out of position. When the groove is shallow, heat sealing is accompanied by damage to the elastic member. In this situation, although there is a possibility that the extension and contraction capabilities of the elastic member is reduced, positioning of the elastic member is further ensured because the elastic member is fusion bonded inclusively together with the two sheet materials.

While the above-described positioning method has been explained with reference to the third and fourth aspects, the same effects are produced when applied to the fifth and sixth aspects of the invention. When applied to the first and second aspects, the positioning method is also advantageous. For example, the positioning method makes it possible to form gathers stably even when a distance between lines of seals, viewed in the CD, is reduced, which enables reduction of the distance in designing the folds formed between lines of seals.

After the fusion joints 5 are formed, the two sheet materials having the elastic members 4 therebetween are subjected to a uniting process for forming the end seals 11 along portions spaced apart in the elastic members 4 extending direction. The uniting process is accomplished by heat embossing or ultrasonic embossing. The uniting process may be a process in which an adhesive is applied to one or both of the two sheet materials and/or the elastic members and the adhesive-applied parts is pressed. When end seals 11 are not formed, the uniting process can be omitted.

The sheet materials 2 and 3 with the elastic members 4 therebetween is then cut across along such positions that the portions having been subjected to the uniting process may be positioned at both ends of the cut part in the elastic members 4 extending direction. The elastic members 4 are let to contract to make each of the sheet materials 2 and 3 create folds. The extensible composite member 1A having the above-described configuration is thus obtained. Where, as in the extensible composite member 1C shown in FIG. 9, an extensible composite member has elastic members 4B that do not pass through the fusion joints 5, the uniting process is particularly preferred to fix the ends of such elastic members.

The fifth and sixth aspects of the present invention will be described based on their preferred embodiments by referring to the accompanying drawings.

Figure 10:
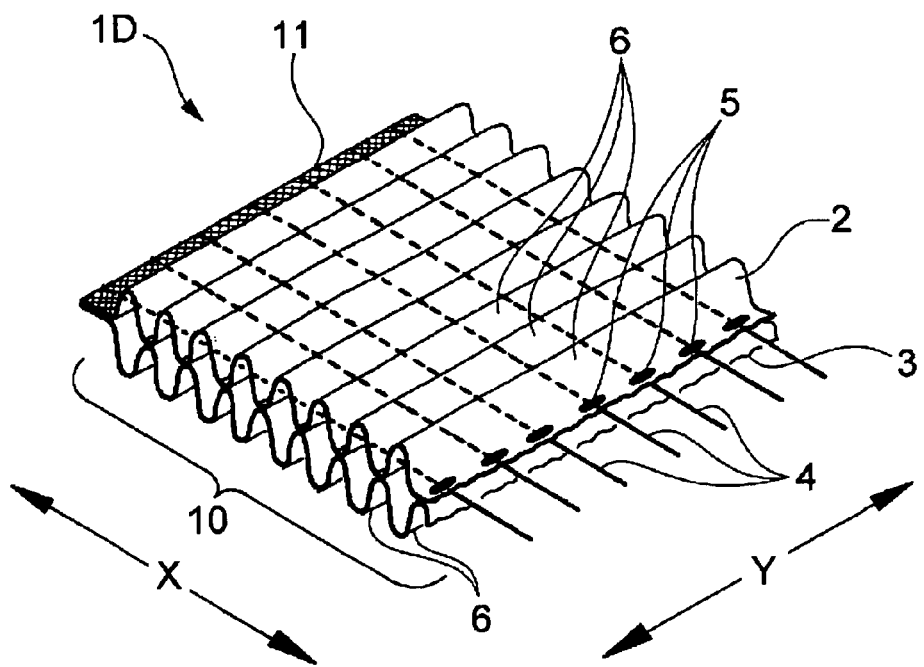
FIG. 10 is a perspective of an extensible composite member according to an embodiment of the fifth aspect of the present invention, with a part cut away.
Figure 11:
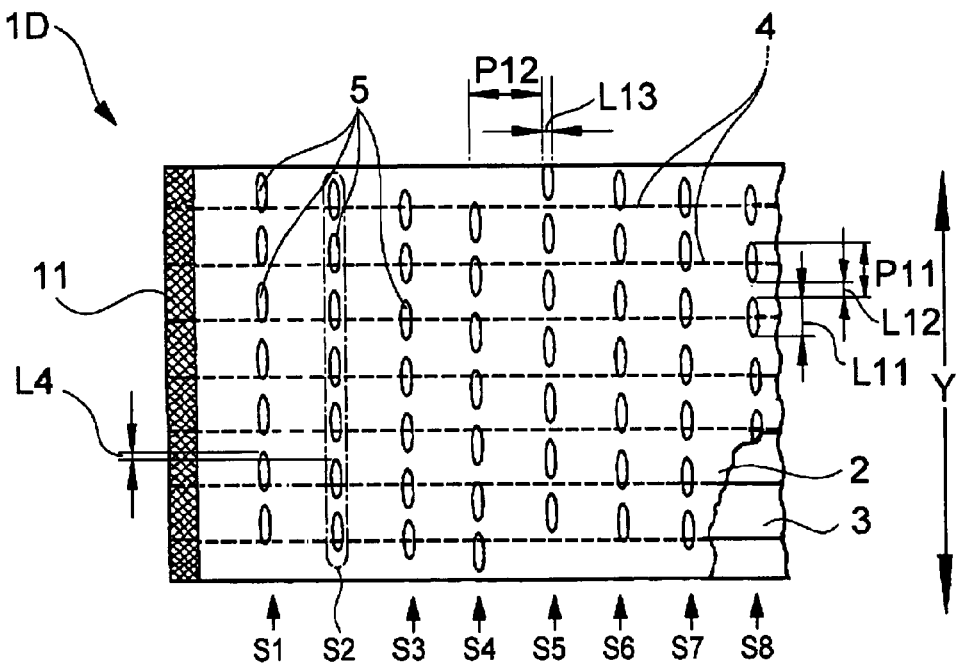
FIG. 11 is a plan of the extensible composite member of FIG. 10 with the elastic members extended to stretch flat.

An extensible composite member 1D as an embodiment of the fifth aspect is composed of two sheet materials 2 and 3 and a plurality of elastic members 4 disposed therebetween as illustrated in FIGS. 10 and 11.

The extensible composite member 1D is rectangular in its plan view. The extensible composite member 1D has an end seal 11 at both ends thereof (only one end is illustrated) in the extending direction (running direction) of the elastic members 4, each end seal 11 being continuous in the direction perpendicular to the elastic members 4 extending direction. All the elastic members 4 are fixed between the sheet materials 2 and 3 in the end seals 11. The portion of the extensible composite member 1D except the end seals 11 is an extensible portion 10.

As illustrated in FIG. 11, the sheet materials 2 and 3 are partly joined together by fusion bonding to form a plurality of joints 5. The joints 5 line up to form a plurality of joint lines (S1 to S8) running in a direction (direction Y) crossing the elastic members 4 extending direction (X direction). In this embodiment, each of the joint lines S1 to S8 is made up of a plurality of joints (a group of joints) spacedly placed in the Y direction.

Figure 13A:
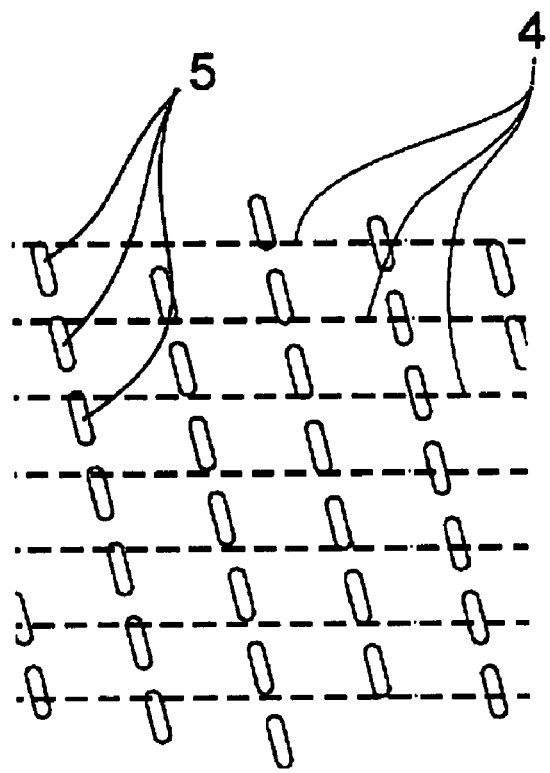
FIG. 13($a$) illustrates a pattern of arranging joints in still another embodiment of the fifth aspect of the present invention, in which the longitudinal direction of the individual joints coincides with the running direction of the joint lines.
Figure 13B:
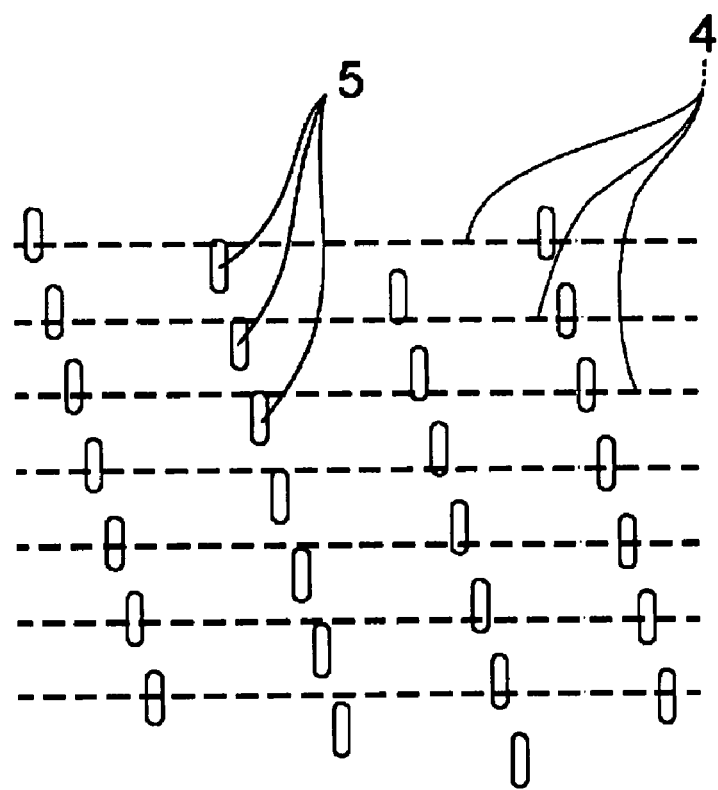

"Direction crossing the elastic members 4 extending direction" as used herein denotes a direction unparallel with the extending direction of the elastic members 4, making a certain angle with the extending direction. In this particular embodiment, the crossing direction is a direction perpendicular to the elastic members 4 extending direction, i.e., Y direction. The crossing angle being taken as 90° when the crossing direction is perpendicular to the elastic members 4 extending direction as in the present embodiment, the crossing direction preferably makes an angle of 75° to 105°, more preferably 85° to 95°, even more preferably 90°. FIGS. 13(a) and 13(b) present other examples of joint lines running in a direction crossing the elastic members 4 extending direction. The joint lines extending in a direction crossing the elastic members 4 extending direction may coincide with the longitudinal direction of the individual joints 5 making up each joint line as in the example shown in FIG. 13(a) or may have an angle with the longitudinal direction of the individual joints 5 making up each joint line as in the example of FIG. 13(b).

In the present embodiment, the elastic members 4 are equally spaced and parallel to each other. When elastic members are parallel with each other, the direction of extension (stretch) and contraction of the elastic members 4 is the same as the running direction of the elastic members 4. When elastic members 4 are not parallel with each other, the elastic members 4 extending and contracting direction is a direction perpendicular to the running direction of folds 6 (hereinafter described).

As illustrated in FIG. 11, the extensible composite member 1D has a plurality of (eight in the embodiment illustrated) joint lines S1 to S8, each composed of a plurality of fusion joints 5, spacedly formed in the elastic members 4 extending direction (X direction). In FIG. 11, only one of the joint lines is indicated by a dashed line. The joint lines are equally spaced and parallel with each other. The joints making up each joint line are equally spaced in the Y direction. In the present embodiment, all the joint lines are equal in the shape and the size of the individual joints and the pitch P11 of the joints per joint line.

As shown in FIG. 11, a part of the joint lines S1 to S8 (specifically, S1 and S6) and another part of the joint lines (specifically, S2 to S5, S7, and S8) are different in positions of the joints 5 making up each joint line in a direction (Y direction) crossing the extending direction (X direction).

Specifically, the positions of the joints composing a joint line in the direction (Y direction) crossing the elastic members 4 extending direction (X direction) change from one end (the left end in FIG. 11) to the other end (the right end in FIG. 11) in the extending direction (X direction).

More specifically, the positions of the joints composing a joint line in the direction (Y direction) crossing the extending direction (X direction) vary from one end to the other end in the elastic members 4 extending direction (X direction) by a given distance in the Y direction.

As shown in FIG. 11, the joints 5 of the joint line SI and those of the joint line S2 are relatively shifted in the direction (Y direction) crossing the extending direction by a distance L4. The same relationship applies to every two adjacent joint lines.

In the present embodiment, every fifth joint line has the joints at the same positions in the Y direction. That is, each pair in the joint lines S1 and S6, the joint lines S2 and S7, and the joint lines S3 and S8 have their joints at the same positions. A plurality of joint lines different from each other in the positions of the joints in the Y direction are formed in such an arrangement that joint lines having their joints at the same positions in Y the direction may appear at every plurality of joint lines (e.g., 2 to 10 joint lines). By arranging the joints at positions shifted by a constant distance, the extensible composite member has a neat appearance, and the stress of the elastic members can be equally applied to each of the two sheet materials.

The distance L4, an amount of displacement of the joints between adjacent joint lines, varies depending on the length of the individual joints but is preferably in a range of from 3% to 50%, more preferably from 5% to 30%, of the pitch P11 of the joints in a joint line from the standpoint of a good visual appeal and equal application of the contraction stress.

To obtain improved flexibility, the ratio of the pitch P11 (see FIG. 11) of the fusion joints 5 in each of the joint lines S1 to S8 to the length L11 (see FIG. 11) of the individual fusion joints 5, P11/L11, preferably ranges from 1.05 to 80, more preferably from 1.05 to 15, and the pitch P11 of the fusion joints is preferably 1 to 40 mm, more preferably 2 to 15 mm.

For the same purpose, it is preferred that the length L11 be 0.5 to 20 mm, more preferably 1 to 10 mm, and that the distance L12 (see FIG. 11) between adjacent fusion joints be 0.5 to 30 mm, more preferably 1 to 20 mm.

In order to form folds 6, especially folds 6 continuously running across a plurality of the elastic members 4 and having a good visual appeal, it is preferred that the joint lines have a pitch P12 (see FIG. 11) of 1 to 30 mm, more preferably 2 to 15 mm and that the individual fusion joints 5 have a length L13 (see FIG. 11) of 0.1 to 5 mm, more preferably 0.2 to 1.5 mm, in the elastic members 4 extending direction (X direction). For the same purpose, the ratio of the pitch P12 to the length L13 (P12/L13) is preferably in the range of from 1.1 to 300, more preferably from 4 to 100.

The above-recited dimensions and ratios are measured with the extensible composite member being in a stretched flat state by stretching the elastic members (a state in which the extensible composite member is stretched out to the same dimension as reached when it is flattened with any influences of the elastic members excluded by, for example, cutting the elastic members) as illustrated in FIG. 11.

Each elastic member 4 is fixed between the sheet materials 2 and 3 at at least a part of the joints 5.

In the present embodiment, every elastic member 4 is fixed between the sheet materials 2 and 3 at joints of a plurality of joint lines. For example, every elastic member 4 shown in FIG. 11 is disposed to overlap the fusion joints 5 making up the joint lines S1 to S4 and the fusion joints 5 making up the joint lines S6 to S8 and fixed between the sheet materials 2 and 3 at each of the overlapping joints 5 without being cut at these joints. The joint lines including the joints at which an elastic member is fixed may be different from the joint lines including the joints at which another elastic member is fixed.

Each elastic member 4 is fixed at the end seals 11 and the joints 5 in its stretched state. The stretch ratio or stretch stress may vary between elastic members 4. For instance, in application as a waist gather band of a pull-on diaper, the elastic member closer to the waist opening (upper elastic member)

can be designed to exert a stronger extension and contraction stress to prevent sliding down without imposing excessive constrictive pressure.

When the extensible composite member 1D of the present embodiment is in a relaxed state (with no external force applied), the elastic members 4 contract, whereby the two sheet materials 2 and 3 each form a plurality of folds 6 between every two adjacent joint lines as shown in FIG. 10.

The folds 6 of the sheets 2 and 3 project on the respective sides of the extensible composite member 1D. Each fold 6 has a curved surface whose cross-section is arc-shaped at the top. Every fold 6 continuously runs in the perpendicular direction (Y direction) across the elastic members 4 without being cut at positions where it crosses the elastic members 4. Therefore, the folds 6 are very beautiful to the eye.

In the present embodiment, since the joint lines S1 to S8 along the direction (Y direction) crossing the elastic members 4 extending direction are each formed of spacedly arranged fusion joints 5, the extensible composite member 1D is very soft and flexible. It is flexibly deformable by, for example, a force compressing the extensible composite member 1D in the Y direction or a force curving the extensible composite member 1D along the Y direction. Therefore, where the extensible composite member 1D is used in an absorbent article as a member making gathers (an extensible portion with a large number of folds), particularly as a member forming standing gathers (standing leakproof cuffs), the gathers are soft and pleasant to the touch and less irritating to the skin.

In the extensible composite member 1D of the present embodiment, the individual elastic members 4 are present between the valleys of every two adjacent folds 6 formed of the sheet material 2 and the valleys of every two adjacent folds 6 formed of the other sheet material 3. Additionally, the folds have a curved surface at the top. Therefore, the extensible composite member 1D has an increased volume in the thickness direction and feels extremely soft and pleasant when touched.

The elastic members 4 used in the extensible composite member 1D of the present embodiment are made of a material capable of developing contraction stress uniformly. Accordingly, the contraction stress of the elastic members 4 can be used to securely gather the two sheet materials between every two adjacent fusion joints. As a result, uniformity that is not to be impaired can be achieved among the folds 6 formed.

Materials that can be used to make the elements constituting the extensible composite member 1D include those described with respect to the extensible composite member 1. Unless inconsistent with the context, the description of the materials making the extensible composite member of the first aspect of the invention applies to the extensible composite member of the fifth aspect.

In the present embodiment, too, the sheet materials 2 and 3 are deformed with the contraction of the elastic members 4 to form folds 6. Similarly to the aforementioned extensible composite member 1, the stiffness of the sheet materials 2 and 3 is an important factor decisive of the fold formability of the extensible composite member and the cushioning properties of the folds formed, and another factor decisive of the fold formability of the extensible composite member is a stretch ratio and a stretch stress of the elastic members. The preferred constitution of the extensible composite member 1 explained above in connection with these factors (e.g., the buckling strength of the sheet materials, the stretch of the elastic members when disposed between the sheet materials, and the height of the folds) also applies to the extensible composite member 1D.

Where nonwoven fabric is chosen as a sheet material, it is preferred to use nonwoven fabric having a weight of 5 to 50 $g/m^2$, more preferably 8 to 30 $g/m^2$. Nonwoven fabric having a weight in that range preferably has a buckling strength of 50 cN or lower, more preferably 30 cN or lower, in the CD and of 70 cN or lower, more preferably 50 cN or lower, in the MD. To use such soft sheet materials secures fold formability.

The above-illustrated extensible composite member 1D is produced efficiently and economically by, for example, the following method.

A plurality of elastic members 4 are disposed in their stretched state between two sheet materials 2 and 3 to prepare a laminate 12 in which the two sheet materials are not joined together. The laminate 12 is partly fusion bonded by heat pressing with projections 7 arranged in the pattern of fusion joints 5 (see FIG. 11) as illustrated in FIG. 7. Care should be taken not to cut the elastic members 4 in the partial heat pressing. In order for the two sheet materials to be fusion bonded together and, at the same time, for the elastic members 4 to be fusion bonded to the sheet materials via the heat fusible fiber present in the sheet materials without being cut, it is preferred to create optimum conditions by controlling three parameters: (1) pressing pressure of the projections 7 to the anvil roll 71, (2) clearance between the projections 7 and the anvil roll 71, and (3) temperature of the projections 7 and the anvil roll 71. It is also effective for preventing the elastic members from being cut to select a material unsusceptible to the influences of pressure and heat, i.e., a cutting-resistant material as elastic members and to set the stretch ratio of the elastic members rather low as the product specification.

It is possible to positively reduce the pressure imposed to the elastic members. Means for reducing pressure application include measures to avoid pressure application to where the projections 7 cross the elastic members. For example, the anvil roll receiving the projections may be made of rubber, e.g., silicon rubber. Where durability of rubber is a problem, rubber may be applied only to the parts on which the elastic members are pressed. Another example is to use projections each having a groove (depression) 72 for pressing pressure reduction along where the elastic member 4 is disposed. Heat fusion using such projections can be effected, e.g., with a heat embosser or an ultrasonic embosser by introducing the laminate 12 into the nip between an embossing roll 70 with the projections 7 on its peripheral surface and a facing anvil roll (backup roll) 71.

The embosser illustrated in FIG. 7 additionally has grooves (depressions) 73 for pressing pressure reduction on the peripheral surface of the anvil roll 71, on which the laminate 12 is pressed under the projections 7, along where the elastic members are disposed.

By making grooves 72 and 73 for pressing pressure reduction on the projections for fusion bonding and/or the facing surface, the elastic members 4 can easily be fixed at the fusion joints 5 without being cut. The part of the elastic member 4 that is fixed in the fusion joint 5 may be merely held between the two sheet materials but with tightness so as not to move between the two sheet materials or may have its surface fusion bonded to one or both of the sheet materials. The grooves for pressing pressure reduction can be provided on either one or both of the projections and facing surface.

After the fusion joints 5 are formed, the two sheet materials having the elastic members 4 therebetween are subjected to a uniting process for forming the end seals 11 along portions spaced apart in the elastic members 4 extending direction. The uniting process is accomplished by heat embossing or ultrasonic embossing. The uniting process may be a process in which an adhesive is applied to one or both of the two sheet materials and/or the elastic members and pressing the adhesive-applied parts. When end seals 11 are not formed, the uniting process can be omitted.

The sheet materials 2 and 3 with the elastic members 4 therebetween is then cut across so that the portions having been subjected to the uniting process may be positioned at both ends of the cut part in the elastic members 4 extending direction. The elastic members 4 are let to contract to make each of the sheet materials 2 and 3 create folds. The extensible composite member 1D having the above-described configuration is thus obtained.

While the present invention has been described with particular reference to its preferred embodiments, the present invention should not be construed as being limited thereto. Examples of alterations or modifications are as follows.

While the folds in the extensible composite members 1 and 1' continuously run between the two elastic members positioned at both Y direction ends, an elastic member at or near one or both of the Y direction ends may be joined to the sheet materials 2 and 3. It is preferred, nevertheless, that the folds runs to bridge across at least three, preferably a half, more preferably 70% or more, of the number of the elastic members. The end(s) of the elastic members 4 joined to the sheet materials 2 and 3 may be inboard of the X direction end(s) of the extensible composite member 1 instead of being at the end portion(s) of the extensible composite member 1.

Figure 8:
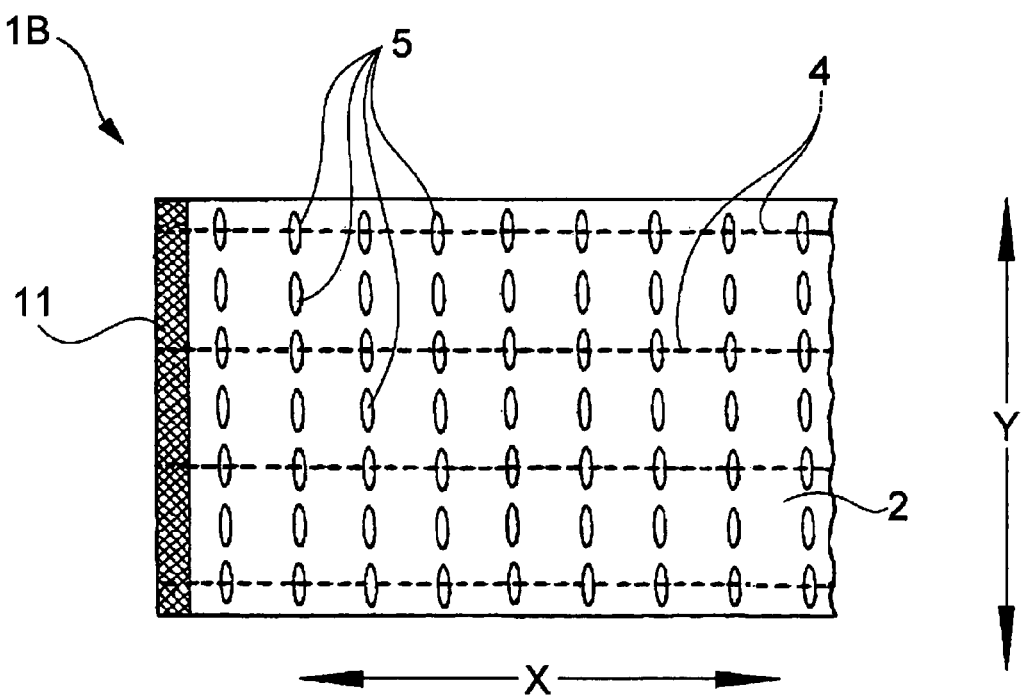
FIG. 8 illustrates an extensible composite member according to another embodiment of the third aspect of the present invention (corresponding to FIG. 6).

In the third aspect of the invention, the number of the elastic members of the extensible composite member does not need to be equal to the number of the joint lines in the elastic members extending direction (X direction). For example, FIG. 8 illustrates an extensible composite member 1B, in which every elastic member 4 overlaps fusion joints 5 forming a joint line in the elastic members 4 extending direction (X direction) but the elastic member 4 is disposed on every second joint line in the extending direction (X direction).

Figure 9:
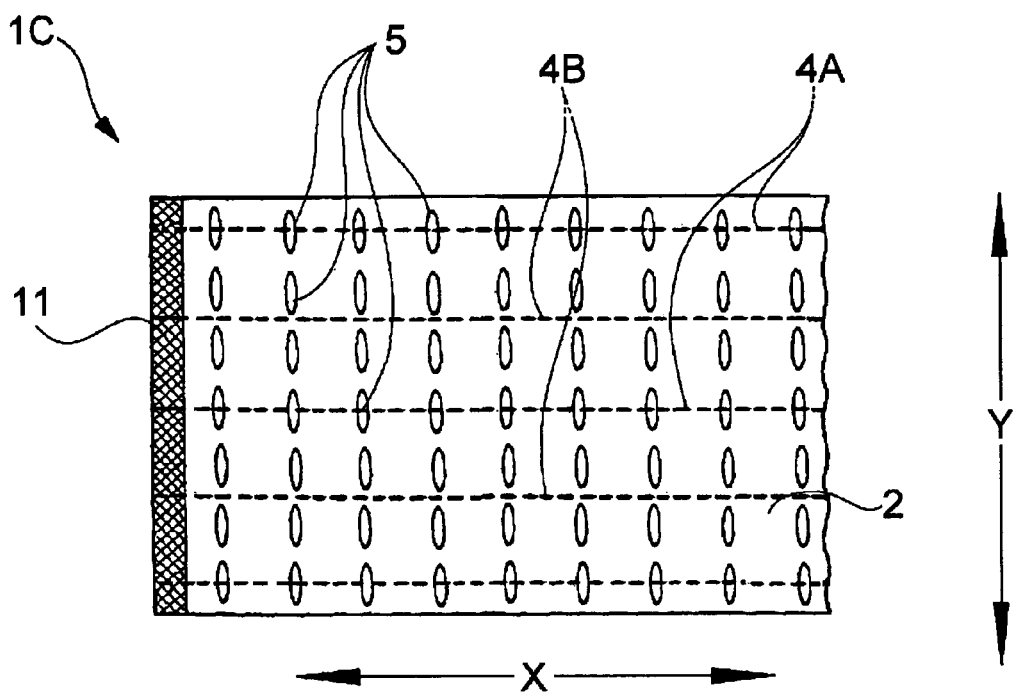
FIG. 9 illustrates an extensible composite member according to still another embodiment of the third aspect of the present invention (corresponding to FIG. 6).

The extensible composite member of the third aspect may have elastic members 4B disposed not to overlap fusion joints, like an extensible composite member 1C illustrated in FIG. 9, in addition to elastic members 4A disposed to overlap fusion joints. The elastic members 4B of the extensible composite member 1C shown in FIG. 9 are fixed to the sheet materials only at the ends seals 11 (only one of which is depicted). It should be noted, however, that at least two of the elastic members disposed in the extensible composite member are fixed at the fusion joints. It is preferred that at least one-third, more preferably at least a half, of the number of the elastic members disposed in the extensible composite member be fixed at the fusion joints. While, in the embodiment shown in FIG. 9, every second elastic member is fixed at fusion joints, every nth (n being a given number), e.g., third or fourth elastic member may be fixed. When both fusion joints having an elastic member fixed therein and fusion joints having no elastic member fixed therein are to be formed, the above-mentioned method of making the extensible composite member is carried out by using an embosser having a groove (depression) for pressing pressure reduction only on a part of the projections for fusion bonding or the surface facing the part of the projections.

The fifth and sixth aspects of the present invention may be implemented as, for example, in the following embodiments.

Figure 12:
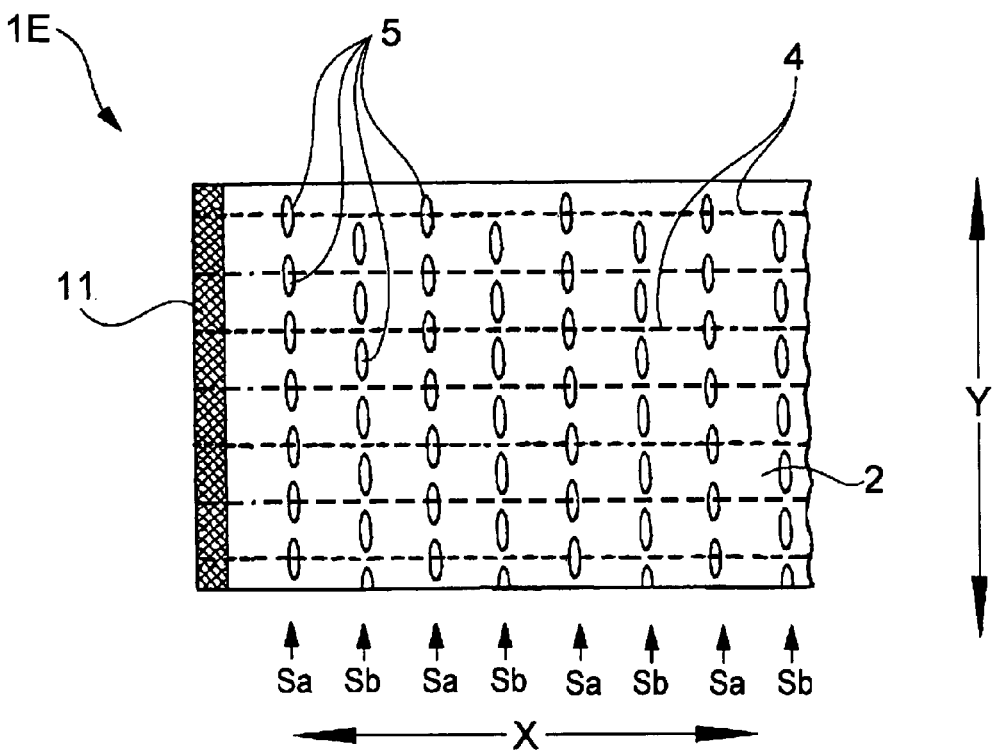
FIG. 12 illustrates an extensible composite member according to another embodiment of the fifth aspect of the present invention (corresponding to FIG. 11).

The configuration in which the positions of joints vary between two or more joint lines may be such that two joint lines Sa and Sb different in the positions of joints alternate as in the embodiment illustrated in FIG. 12.

The pitch of the joints may vary between joint lines. The distance between adjacent joint lines does not need to be constant. The elastic members 4 do not need to be equally spaced. For instance, the extensible composite member may have a group of elastic members spaced at a relatively small interval and a group of elastic members spaced at a relatively large interval, or the interval between adjacent joint lines may be gradually or stepwise increased from one endmost elastic member to the other endmost elastic member. In this way, by altering the arranging interval of the elastic members or the kind and/or stretch ratio of the elastic members as desired, allocation of the contraction stress of the elastic members can be controlled as designed to provide an article, such as a pull-on disposable diaper, with improved performance. In application to pull-on disposable diapers, while not illustrated in the drawing, the gathers provided below a waist gather can be designed to exert a stronger contraction stress in an about 10 mm to 80 mm area thereof along the joint lines than in the other area. A diaper so designed constricts the effective part of a wearer's body for preventing the diaper from sliding down thereby providing an improved body fit.

Figure 14:
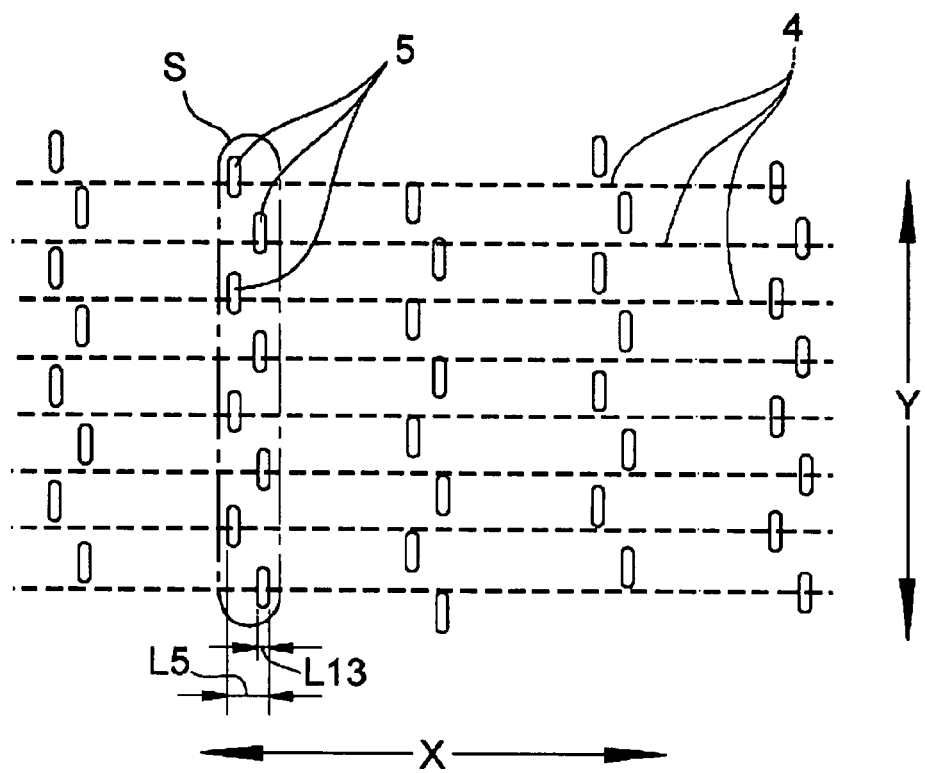
FIG. 14 illustrates a pattern of arranging joints in still another embodiment of the fifth aspect of the present invention.
Figure 15:
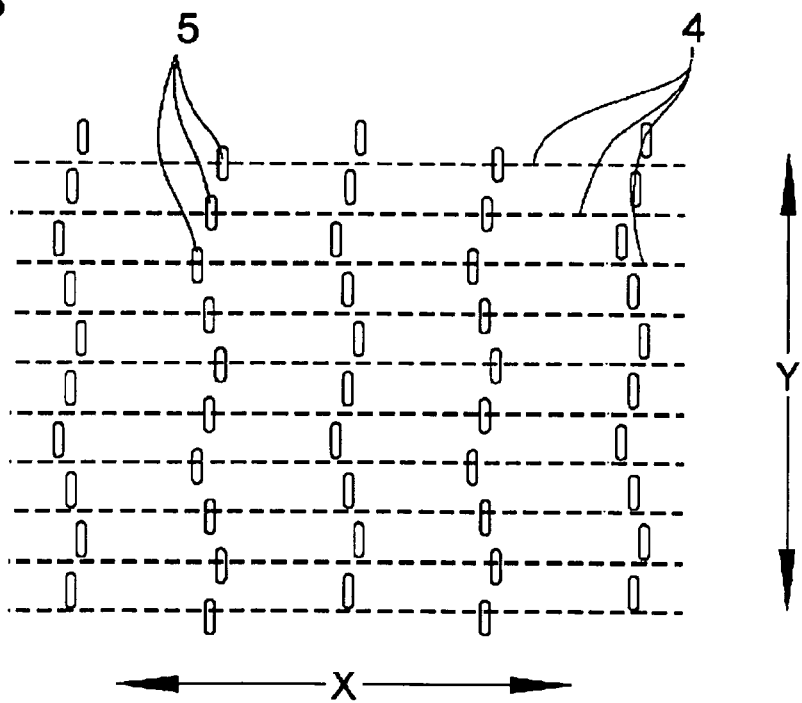
FIG. 15 illustrates a pattern of arranging joints in still another embodiment of the fifth aspect of the present invention.

As illustrated in FIGS. 14 and 15, the joints 5 composing each joint line S may be dispersed to some extent in the width direction of the joint line. It is preferred, nevertheless, that the width L5 (see FIG. 14) of the joint line S in the elastic members extending direction (X direction) be 1.0 to 50 times the length L13 of the individual joints 5 in the elastic members extending direction (X direction). For instance, the width L5 of each joint line S may be 1.0 to 20 times, 1.0 to 10 times, or 1.0 to 5 times, the length L13 of the individual joints 5. The breadth of dispersion of joints 5 in one joint line S (equal to the width of the joint line) is preferably not more than ¼, more preferably not more than ½₀, the distance from the joint line to either of adjacent joint lines. In the embodiment shown in FIG. 14, the joints in each joint line are aligned in a staggered formation. In the embodiment shown in FIG. 15, the joints in each joint line are aligned in a wavy formation. Whichever of the patterns shown in FIGS. 13(a), 13(b), 14, and 15 the joints take on, there will be obtained the same action and effect as with the extensible composite member 1D.

In the present invention inclusive of the first to sixth aspects, the number of the elastic members in an extensible composite member is decided as appropriate to the dimension and use of the extensible composite member. It is selected from, for example, a range of 5 to 30. The joints between the sheet materials formed by fusion bonding may be replaced with those formed by adhering the sheet materials with, e.g., a hot-melt adhesive. The pattern of forming the fusion joints can be altered as appropriate. The shape of the individual fusion joints is appropriately chosen from a rectangle, an elongated circle, a circle, a diamond, and so forth.

The extensible composite members according to the first, third, and fifth aspects of the present invention are especially suited to make extensible portions of absorbent articles, such as disposable diapers and sanitary napkins. In these applications, a separately prepared extensible composite member may be fixed to an absorbent article to provide an absorbent article having an extensible portion. Alternatively, the steps for making an extensible composite member may be incorporated into the production line of an absorbent article to produce an absorbent article having an extensible composite member incorporated therein.

Figure 4:
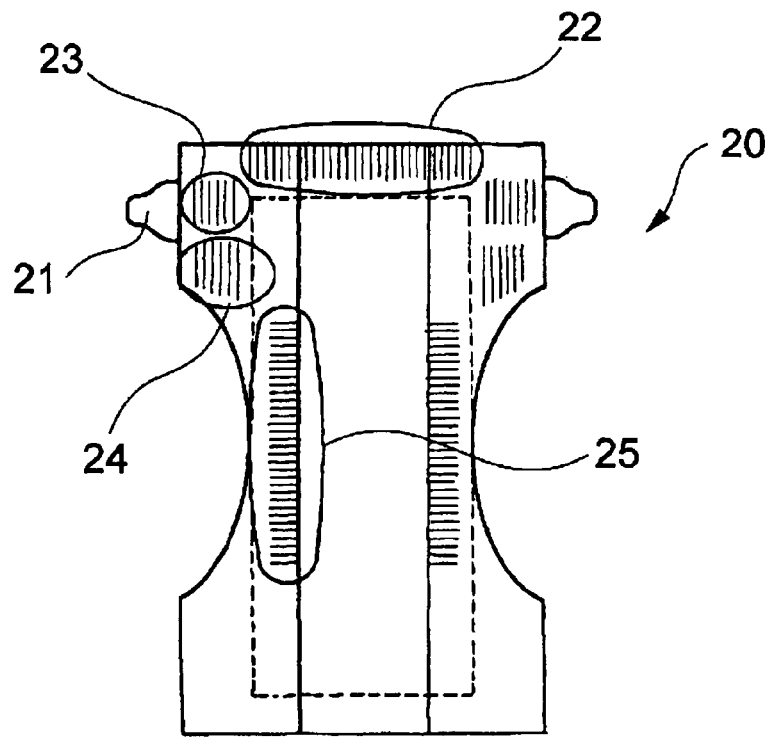
FIG. 4 illustrates extensible portions formed of the extensible composite members according to the first, the third, and the fifth aspects of the present invention, applied to a disposable diaper with fastening tapes.

FIG. 4 illustrates extensible portions formed of extensible composite members, taking for instance a disposable diaper 20 with fastening tapes 21. The extensible composite member of the present invention can be used to make, for example, a waist extensible portion 22, a fastening tape-neighboring extensible portion 23 that extends and contracts with the fastening tape 21, a below-waist extensible portion 24, and an extensible portion 25 formed on the skin-contact side of a standing anti-leak cuff, and the like.

INDUSTRIAL APPLICABILITY

The extensible composite member according to the first aspect of the invention has gathers (an extensible portion with many folds) soft to the touch and beautiful to the eye, and provides an absorbent article, etc. with such gathers.

The method of making an extensible composite member according to the second aspect of the invention provides with ease an extensible composite member having gathers (an extensible portion with many folds) soft to the touch and beautiful to the eye.

The extensible composite members according to the third and fifth aspects of the invention have gathers (an extensible portion with many folds) which are flexible, soft and smooth to the touch, and provide an absorbent article, etc. with such gathers.

The methods of making an extensible composite member according to the fourth and sixth aspects of the invention provide with ease an extensible composite member having gathers (an extensible portion with many folds) which are flexible, soft and smooth to the touch.

The invention claimed is:

1. An extensible composite member having an extensible portion comprising two sheet materials and a plurality of elastic members intermediate between the sheet materials,
    the two sheet materials being discontinuously bonded to each other at joints in the extending direction of the extensible portion and a direction perpendicular to the extending direction of the extensible portion,
    the elastic members being arranged in the extensible portion avoiding the joints between the sheet materials and having both ends thereof fixed to the sheet materials,
    each of the two sheet materials forming a plurality of folds continuously running across a plurality of the elastic members.

2. The extensible composite member according to claim 1, wherein the joints between the two sheet materials are formed by fusion bonding the sheet materials.

3. The extensible composite member according to claim 1, wherein the joints between the sheet materials are arranged in a staggered pattern, have a pitch P1 of 1 to 30 mm and each have a length L1 of 0.1 to 5 mm both measured in the extending direction of the extensible portion with the extensible portion being in the extended state, and the ratio of the pitch P1 to the length L1 (P1/L1) ranges from 1.1 to 300.

4. The extensible composite member according to claim 1, wherein the joints between the sheet materials are arranged to line up in both the extending direction of the extensible portion and a direction perpendicular thereto, the joints lining in the perpendicular direction are placed between every two adjacent elastic members, the joints have a pitch P2 of 1 to 20 mm and each have a length L2 of 0.1 to 5 mm both measured in the extending direction of the extensible portion with the extensible portion being in the extended state, and the ratio of the pitch P2 to the length L2 (P2/L2) ranges from 1.1 to 200.

5. A method of making the extensible composite member according to claim 1, comprising the steps of:
    arranging a plurality of elastic members in their stretched state on a first sheet material and superposing a second sheet material on the side of the first sheet material having the elastic members on,
    partly joining the first and second sheet materials in their superposed state in an area where the elastic member is absent,
    subjecting the first and the second sheet materials with the elastic members therebetween to a process for fixing the elastic members to the first and the second sheet materials along portions spaced apart from each other in the extending direction of the elastic members, and
    allowing the elastic members to contract to cause each of the first and the second sheet materials to form a plurality of folds.

6. An extensible composite member comprising two sheet materials and a plurality of elastic members intermediate between the sheet materials,
    wherein the sheet materials being discontinuously bonded to each other in the extending direction of the elastic members and a direction perpendicular thereto to form a plurality of joint lines each composed of a plurality of joints in each of the two directions,
    the joint lines in the direction crossing the extending direction each have a ratio of a pitch P11 of arranging the fusion joints to a length L11 of the individual fusion joints (P11/L11) ranging from 1.05 to 80, and the pitch P11 of arranging the fusion joints is 1 to 40 mm,
    at least two of the elastic members being disposed along the joint lines in the extending direction to overlap each of the joints composing the respective joint lines and fixed between the sheet materials at the individual joints, and
    the sheet materials each forming folds between the joint lines in the direction perpendicular to the extending direction.

7. The extensible composite member according to claim 6, wherein the joints between the two sheet materials are formed by fusion bonding the sheet materials.

8. A method of making the extensible composite member according to claim 6, comprising the steps of disposing a plurality of elastic members in their stretched state between two sheet materials and partly heat-pressing the superposed sheet materials with a plurality of projections to partly fusion bond the sheet materials to form the joints,
    the step of partly heat-pressing being carried out in a manner that does not result in cutting the elastic members.

9. An extensible composite member comprising two sheet materials and a plurality of elastic members disposed between the sheet materials,
    wherein the two sheet materials being partly bonded to each other to form joints,
    the joints lining up to make joint lines in a direction crossing the extending direction of the elastic members,
    a part of the joint lines and another part of the joints being different in positions of the joints making up each joint line in the direction crossing the extending direction,
    the ratio of the pitch P11 of the fusion joints in the individual joint lines to the length L11 of the individual fusion joints in the joint lines (P11/L11) ranges from 1.05 to 80, and the pitch P11 of the fusion joints is 1 to 40 mm,
    the elastic members being each fixed between the sheet materials at least part of the joints, and
    the sheet materials each forming folds between every two adjacent joint lines.

10. The extensible composite member according to claim 9, wherein the width of the joint line in the extending direction of the elastic members is 1.0 to 50 times the length of the individual joints in the extending direction of the elastic members.

11. The extensible composite member according to claim 9, wherein the positions of the joints composing the individual joint lines in a crossing direction crossing the extending direction of the elastic members vary from one end to the other in the extending direction of the elastic members by a given distance in the crossing direction.

12. The extensible composite member according to claim 11, wherein the positions of the joints composing the individual joint lines in a crossing direction crossing the extending direction of the elastic members vary from one end to the other in the extending direction by a distance corresponding to 3% to 50% of the pitch of the joints in the joint lines.

13. The extensible composite member according to claim 9, wherein the joints are formed by fusion bonding the two sheet materials.

14. A method of making the extensible composite member according to claim 9, comprising the steps of disposing a plurality of elastic members in their stretched state between two sheet materials and partly heat-pressing the superposed sheet materials with a plurality of projections to partly fusion bond the sheet materials to form the joints, the step of partly heat-pressing being carried out in a manner that does not result in cutting the elastic members.

* * * * *